United States Patent [19]

Quadro

[11] 4,221,805
[45] Sep. 9, 1980

[54] METHOD OF INDUCING PLATELET ANTIAGGREGATION ACTIVITY

[76] Inventor: Giuseppe Quadro, Via Cappuccini 20, Milan, Italy

[21] Appl. No.: 927,726

[22] Filed: Jul. 24, 1978

[51] Int. Cl.$^2$ ............................................. A61K 31/40
[52] U.S. Cl. ..................................................... 424/274
[58] Field of Search ......................................... 424/274

[56] References Cited

FOREIGN PATENT DOCUMENTS 268094  5/1950  Switzerland ......................... 424/274 X

OTHER PUBLICATIONS

Chem. Abst. vol. 60, No. 499b pp. 496–500, 1963, Erdtman et al.

Chem. Abst., vol. 79, No. 133,415s, p. 70, 1973, McDonald et al.

*Primary Examiner*—Anna P. Fagelson
*Attorney, Agent, or Firm*—Bucknam and Archer

[57] ABSTRACT

Compositions useful for platelet antiaggregation activity are described, which contain as the active ingredient N-(2-chlorobenzyl)-pyrrolidine or a pharmacologically compatible salt thereof with an organic or an inorganic acid, and at least one pharmaceutically acceptable carrier or excipient. The compositions in the form of an aqueous solution are administered orally in the dose of 2–8 mgs/kg, preferably 3 mgs/kg body weight twice a day. The compositions may also be administered intravenously or endoperitoneally. The compositions may be administered in the form of capsules, ampoules or in the form of oily suspensions, solutions or emulsions.

7 Claims, No Drawings

METHOD OF INDUCING PLATELET ANTIAGGREGATION ACTIVITY

This invention relates to a drug with platelet anti-aggregation activity.

According to the present invention I provide a pharmaceutical composition for internal administration, comprising N-(2-chlorobenzyl)-pyrrolidine or a pharmacologically compatible salt thereof with an organic or inorganic acid, together with a pharmaceutical carrier or excipient.

The compound according to the inventions is described in Swiss Pat. No. 268,694 (see C.A. 45, 4399). This patent claims that it is possible to use a range of compounds of a general formula which includes N-(2-chlorobenzyl)-pyrrolidine, as acaricides.

It has now been surprisingly found that the compound possesses an important platelet aggregation inhibition activity, and at the same time a very low toxicity. These two characteristic allow it to be used in cerebral vasculopathy therapy.

The compound can be obtained by reacting pyrrolidine with 2-chlorobenzyl chloride, or by reducing N-(2-chlorobenzoyl)-pyrrolidine. The two preparative methods are illustrated in the examples given hereinafter.

EXAMPLE 1

A solution of 50 g of 2-chlorobenzyl chloride in 100 ml of toluene is added in portions under agitation to a solution of 55 g of pyrrolidine in 150 ml of toluene, maintaining the temperature below 40° C. When all has been added, the mixture is brought to boiling point and heated under reflux for three hours. After cooling, it is washed twice with water, the toluene solution is dried over $K_2CO_3$, and the solvent is removed under reduced pressure. The residue is distilled under vacuum. B.P.=102°-104° C. 46 grams of N-(2-chlorobenzyl)-pyrrolidine are obtained. The analytical and spectral (I.R., N.M.R.) data agree with the proposed formula. Treating a solution in ether with gaseous HCl gives the hydrochloride, M.P. 170° C.

EXAMPLE 2

By reducing N-(2-chlorobenzoyl)-pyrrolidine (obtained from 2-chlorobenzoyl chloride and pyrrolidine in a molar ratio of 1:2.2) with aluminium and lithium hydride in anhydrous ether, a product identical to that prepared under example 1 was obtained with a yield of 86%.

The pharmacological interest of the compound according to the invention is documented by the experiments summarised hereinafter, in which N-(2-chlorobenzyl)-pyrrolidine hydrochloride is designated by the symbol $MRAP_2$.

(1) Acute toxicity in mice

A total of 240 albino mice, 120 male and 120 female, of the Swiss strain and having an average weight of about 20 grams were used. The animals were divided into groups of 10 animals each, and kept caged for some days in an environment at a constant temperature (21°±1° C.) and humidity (60±5%). They were then fasted for 24 hours before the experiment, but were given free access to water.

The substance indicated by $MRAP_2$ was administered, in a single administration, either orally or endoperitoneally. The $LD_{50}$ was evaluated for each of the administration methods, using the method of Litchfield and Wilcoxon, J.Pharmacology, 96, 99, 1974, based on the mortality recorded for each group of mice over the seven days following administration.

$LD_{50}$ for oral administration

Six groups of 20 animals, 10 male and 10 female, which had been given $MRAP_2$ dissolved in tap water were used, the method utilised being gastric catheterisation.

The $LD_{50}$ was 536 mg/kg (Table 1).

$LD_{50}$ for endoperitoneal administration

Six groups of 20 animals, 10 male and 10 female, which had been given the active principle dissolved in a physiological solution were used. The $LD_{50}$ was 116 mg/kg (Table 2).

(2) Acute toxicuty in rats 200 albino rats, 100 male and 100 female, of the Wistar strain and weighing 130-150 grams were divided into groups of 10 animals each.

After being caged for some days at constant temperature (21°±1° C.) and humidity (60±5%), the animals were fasted for 24 hours before treatment.

The $MRAP_2$ was administered in a single administration either orally or endoperitoneally, following the method heretofore described.

Teh $LD_{50}$ was evaluated for each method of administration using the Litchfield and Wilcoxon method, based on the percentage mortality recorded in each group of rats during the seven days following treatment.

$LD_{50}$ for oral administration

Five groups of 20 animals, 10 male and 10 female were used. The $LD_{50}$ was 675 mg/kg (Table 3).

$LD_{50}$ for endoperitoneal administration

Five groups of 20 animals, 10 male and 10 female were used. The $LD_{50}$ was 188 mg/kg (Table 4).

(3) Effect on the cardiovascular system of cats

Three cats weighing 2.4-2.6 kg were used for this test. The $MRAP_2$ was administered intravenously in a dose of 5 mg/kg, carried in a sterile physiological solution.

The animals, under combined anaesthesia with ethylurethane and diallylbarbituric acid, were subjected to measurements, by means of the Battaglia-Rangoni polygraph, of the arterial pressure, the cardiac frequency, the nictitation and the electrocardiac activity, before and up to two hours after the administration of the drug.

The results show that the drug in question, apart from a slight hypertensive effect in the four minutes following the introduction of the drug, does not give rise to any undesirable effects on the cardiovascular system.

(4) In vitro platelet antiaggregation activity

The method described by Born (Nature, 194, 927, 1962) was followed for this test, based on the increase in the platelet aggregation induced by ADP. The experiment was conducted using a human PRP (Platelet Rich Plasma) pool from four healthy volunteers who had not taken any drugs for ten days. The PRP was adjusted to 280,000±20,000 and kept at ambient temperature for the entire duration of the test.

400 μl of PRP and 100 μl of MRAP$_2$ dissolved in a physiological solution and adjusted to a pH of 7.4 were placed in plastic test tubes. Three doses of the drug in question (0.181, 0.904 and 1.818 mg/ml) were used.

Three dilutions of aspirin were prepared under the same conditions for use as a comparison drug. Two minutes after contact between the drug and PRP, the test tube was inserted into the aggregometer cell (EEI, Model 169 with Corning Recorder Mod.840). After 60 seconds, ADP ($10^{-3}$mM) was added and the aggregation was recorded. In calculating the antiaggregation activity, reference was made to the maximum amplitude of the aggregation curved obtained with ADP. Assuming this amplitude to be 100, the amplitudes of the curves obtained with the various doses of MRAP$_2$ and aspirin were calculated as a percentage. Table 5 shows that the MRAP$_2$ possesses considerable platelet antiaggregation activity, manifested by the dose of 0.904 mg/ml.

This activity is clearly superior to that possessed by aspirin.

(5) In vivo platelet antiaggregation activity

This experiment was carried out on male rats of the Wistar strain having a weight of 320±20 grams. Both the MRAP$_2$ and the aspirin (used as a comparison drug) were dissolved in a physiological solution, and the solutions, adjusted to pH 7.4, were administered orally in doeses of 3 mg/kg to two groups of three rats each. One group of three animals was kept for control purposes and did not receive any treatment. The concentration of the solution was adjusted to contain 100 mg of MRAP$_2$ per ml.

Blood samples were drawn from each animal 72 and 120 hours after treatment, for checking the platelet aggregation.

In calculating the activity, the previous method was used (the average of the three maximum amplitudes of the curves obtained with the untreated rats was given the control figure of 100%).

The results, shown in Table 6, show that the antiaggregation activity of MRAP$_2$ is superior to that of aspirin, when tested in vivo.

(6) Ulcerogenic activity in rats

The ulcerogenic activity of MRAP$_2$ was tested both after a single administration of the drug, and after prolonged administration.

In these tests, a total of 70 male albino rats of Wistar strain were used, having a weight of 200±20 grams.

The MRAP$_2$ was administered diluted in tap water.

(a) After a single administration 40 rats, fasted for 18 hours before the experiment, were divided into four batches of ten animals and treated orally as follows:
  1st group: controls
  2nd group: phenylbutazone (100 mg/kg)
  3rd group: MRAP$_2$ (50 mg/kg)
  4th group: MRAP$_2$ (125 mg/kg).

The phenylbutazone was administered as a comparison drug, carried in 2% carboxymethylcellulose in tap water.

The animals were killed after six hours. The stomach was withdrawn and the gastric lesion index was evaluated in terms of an arbitrary scale of values lying between 0. and 7 based on previous models proposed by other authors.

The evaluation of the degree of lesion was made by an observer who was not informed as to the treatment to which the individual groups had been subjected. Furthermore, the treatment was randomised in order to eliminate any possible polarisation of the data. For this purpose, a number was assigned to each pair of animals, and the key was revealed only at the end of the readings.

The points given for gastric ulcerative lesions were as follows:

(0) no lesion;
(1) hyperaemia or slight capillary obstruction; or slight loss of the epithelium; or some petechiae even with pale mucosa without hyperaemia;
(2) diffuse capillary obstructions or numerous petechiae; or diffuse loss of the epithelium; of a few surface lesions;
(3) strong submucosa haemorrhage; or many petechiae and small surface lesions; or much anaemic mucosa (yellowish colour); or up to three small ulcers;
(4) general pattern as in the previous numbers, plus up to ten small ulcers; or long erosions; or up to three medium sized ulcers;
(5) pattern as in number 4, with up to 15 small ulcers; or up to 6 large ulcers;
(6) pattern as previously, with up to ten large ulcers, plus small ulcers;
(7) pattern as previously, plus up to ten large ulcers and small ulcers; cases of perforated ulcers.

The results obtained are shown in Table 7. From this, it can be seen that the incidence of ulcerative lesions, which is very marked in the case of 100 mg/kg of phenylbutazone (6.35), is almost identical or slightly greater than that of the control animals in the case of treatment with MRAP$_2$.

(b) After prolonged administration

30 Rats were divided into three batches of ten animals each, and subjected daily over a period of six days to the following oral treatment:
  1st group: controls
  2nd group: MRAP$_2$ (50 mg/kg)
  3rd group: MRAP$_2$ (125 mg/kg)

Six hours after the last treatment, the animals were killed and the lesion index was evaluated following the techniques and methods previously described.

The results, given in Table 8, indicate that MRAP$_2$ possesses an ulcerogenic activity which is significant only at a dose of 125 mg/kg, but even then only slight.

TABLE 1

| | LD$_{50}$ in mice after oral administration of MRAP$_2$ | | | |
|---|---|---|---|---|
| Dose mg/kg | No. of animals per dose | No. of animals dead | % mortality | LD$_{50}$ (limits of reliability 95%) |
| 1000 | 20 | 20 | 100 | |
| 800 | 20 | 20 | 100 | |
| 600 | 20 | 12 | 60 | 536 |
| 500 | 20 | 9 | 45 | (515-561) |
| 400 | 20 | 4 | 20 | |
| 300 | 20 | 0 | 0 | |

TABLE 2

LD$_{50}$ in mice after endoperitoneal administration of MRAP$_2$

| Dose mg/kg | No. of animals per dose | No. of animals dead | % mortality | LD$_{50}$ (limits of reliability 95%) |
|---|---|---|---|---|
| 400 | 20 | 20 | 100 | |
| 300 | 20 | 20 | 100 | |
| 200 | 20 | 20 | 100 | 116 |
| 150 | 20 | 18 | 90 | (105–130) |
| 100 | 20 | 2 | 10 | |
| 75 | 20 | 0 | 0 | |

TABLE 3

LD$_{50}$ in rats after oral administration of MRAP$_2$

| Dose mg/kg | No. of animals per dose | No. of animals dead | % mortality | LD$_{50}$ (limits of reliability 95%) |
|---|---|---|---|---|
| 1000 | 20 | 20 | 100 | |
| 800 | 20 | 15 | 75 | 675 |
| 600 | 20 | 8 | 40 | (631–714) |
| 500 | 20 | 4 | 20 | |
| 400 | 20 | 0 | 0 | |

TABLE 4

LD$_{50}$ in rats after endoperitoneal administration of MRAP$_2$

| Dose mg/kg | No. of animals per dose | No. of animals dead | % mortality | LD$_{50}$ (limits of reliability 95%) |
|---|---|---|---|---|
| 400 | 20 | 20 | 100 | |
| 300 | 20 | 17 | 85 | 188 |
| 200 | 20 | 11 | 55 | (174–203) |
| 100 | 20 | 1 | 5 | |
| 50 | 20 | 0 | 0 | |

TABLE 5

Platelet antiaggregation activity in vitro

| Drug | Dose mg/ml | Platelet aggregation % | Platelet antiaggregation activity % |
|---|---|---|---|
| Serum + physiological ADP | — | 100 | — |
| Serum + ADP MRAP$_2$ | 0.181 | 74 | 26 |
| Serum + ADP MRAP$_2$ | 0.904 | 9 | 91 |
| Serum + ADP MRAP$_2$ | 1.818 | 8 | 92 |
| Serum + ADP aspirin | 0.181 | 95 | 5 |
| Serum + ADP aspirin | 0.904 | 37 | 63 |
| Serum + ADP aspirin | 1.818 | 26 | 74 |

TABLE 6

Platelet aggregation in vivo

| Treatment | Dose mg/kg | % platelet aggregation on day 3 | % platelet aggregation on day 5 | % platelet antiaggregation activity on day 3 | % platelet antiaggregation activity on day 5 |
|---|---|---|---|---|---|
| Controls | — | 100 | 100 | — | — |
| MRAP$_2$ | 3 | 62 | 63 | 38 | 37 |
| Aspirin | 3 | 75 | 75 | 25 | 25 |

N.B. Both MRAP$_2$ and aspirin were administered orally in a single dose of 3 mg/kg at the beginning of the experiment.

TABLE 7

Ulcerogenic activity of MRAP$_2$ after a single administration in rats

| Treatment | Dose mg/kg | Average degree of lesion ± E.E. |
|---|---|---|
| Controls | — | 0.65 ± 0.1 |
| Phenylbutazone | 100 | 6.35 ± 0.2* |
| MRAP$_2$ | 50 | 0.80 ± 0.1 |
| MRAP$_2$ | 125 | 1.15 ± 0.2* |

*P <0.05 with regard to controls.

TABLE 8

Ulcerogenic activity of MRAP$_2$ after prolonged administration in rats

| Treatment | Dose mg/kg | Average degree of lesion ± E.E. |
|---|---|---|
| Controls | — | 0.57 ± 0.1 |
| MRAP$_2$ | 50 | 0.86 ± 0.2 |
| MRAP$_2$ | 125 | 1.07 ± 0.2* |

*P <0.05 with regard to controls.

The compositions of the invention which have platelet antiaggregation activity may be formed into various pharmaceutical preparations such as preparations for injection, oral administration and suitable preparation forms may be decided appropriately depending on the intended administration method. Specifically, water-soluble liquid and oil preparations for injection may be formed using N-(2-chlorobenzyl)-pyrrolidine as the effective ingredient according to ordinary methods adopted in the pharmaceutical industry, and preparations for oral administration, such as capsules and tablets, may also be formed according to methods ordinarily adopted in the pharmaceutical industry.

In pharmaceutical preparations of the compositions of the present invention, N-(2-chlorobenzyl)-pyrrolidine or one of its salts as the active ingredient may be formed into aqueous or oily suspensions, solutions or emulsions which are used for subcutaneous or intravenous injection.

The dosage for human adults is varied to some extent depending on the administration course and frequency, but in general, a preferred daily dose orally is about 2 mg–8 mg of the active ingredient per kg of the body weight twice a day. The administration is continued for a period of 30–120 days. When N-(2-chlorobenzyl)-pyrrolidine is formed into liquid preparations for injection, it is provided in the form of ampoules containing a unit amount for administration, that is 100 mg/ml. These preparations may be suspensions, solutions and emulsions in oily or aqueous vehicles, and additives such as suspending agents, stabilizers and dispersants may be incorporated into these preparations. As the suspending agent, there can be used, for example, glucose, gelatin and aluminium stearate gel, and as the stabilizer, there can be used, for example, lecithin.

In general, the preparation contains about 25 to 100 g of N-(2-chlorobenzyl)-pyrrolidine in 1000 ml of physiological saline solution.

When N-(2-chlorobenzyl)-pyrrolidine is orally administered, it is preferred that it be administered in the form readily absorbable from the intestinal tract, for example, in the form of hydrochloride.

Binders such as gelatin and sorbitol, excipients such as lactose, sucrose, starch and glycine, stabilizers such as magnesium stearate and absorbic acid, and distintegration such as potato starch are optionally used for formation of capsules for oral administration. In general, the capsule contains about 50–200 mg of N-(2-chlorobenzyl)-pyrrolidine. The compositions of the present invention may be administered to humans as well as animals and lower animals such as rats, mice and guinea pigs.

What is claimed is:

1. The method of inducing platelet antiaggregation activity in a living subject in need of said treatment which consists of administering to said subject a composition comprising an effective amount therefor of the active ingredient N-(2-chlorobenzyl)-pyrrolidine or the hydrochloride salt thereof.

2. The method according to claim 1 wherein said composition is administered orally, intravenously or endoperitoneally.

3. The method according to claim 1 wherein the composition is administered orally twice a day in the amount of 2-8 mg of said active ingredient per kg of body weight in the form of an aqueous solution.

4. The method according to claim 3 wherein the composition is administered in the form of an aqueous solution containing a unit amount of 100 mg/ml of said active ingredient.

5. The method according to claim 3 wherein said active ingredient is the hydrochloride salt of N-(2-chlorobenzyl)-pyrrolidine.

6. The method according to claim 3 wherein said composition is administered in a dose of 3 mg of said active ingredient per kg of body weight twice a day.

7. The method according to claim 6 wherein said composition is administered orally for a period of 30-120 days.

* * * * *